United States Patent [19]

Vaseen

[11] 4,232,665
[45] Nov. 11, 1980

[54] PORTABLE LUNG APPARATUS

[76] Inventor: Vesper A. Vaseen, 9840 W. 35th Ave., Wheatridge, Colo. 80033

[21] Appl. No.: 2,459

[22] Filed: Jan. 10, 1979

Related U.S. Application Data

[63] Continuation-in-part of Ser. No. 808,286, Jun. 20, 1977, abandoned.

[51] Int. Cl.$^3$ .............................................. A61M 16/00
[52] U.S. Cl. ................................ 128/200.24; 128/913
[58] Field of Search .................... 128/172, 188, 207.28, 128/200.24, 913; 424/366

[56] References Cited

FOREIGN PATENT DOCUMENTS 2253534  5/1973  Fed. Rep. of Germany ... 128/DIG. 31

OTHER PUBLICATIONS

Patel et al., Survival and Histopathologic Changes in Lungs of Hamsters Following Synthetic Liquid Breathing, Fed. Proc. vol. 29, No. 5, Oct. 1970, pp. 1740–1745.
Moskowitz, A Mechanical Respirator for Control of Liquid Breathing, Fed. Proc. vol. 29, No. 5, Oct. 1970, pp. 1751–1752.
Rahn, Discussion on Liquid Breathing, Fed. Proc. vol. 29, No. 5, pp. 1753–1754, Oct. 1970.
Clark, Jr. et al., Perfusion of Whole Animals with Perfluorinated Liquid Emulsions Using the Clark Bubble-Defoam Heart Lung Machine, Fed. Proc. vol. 29, No. 5, pp. 1764–1770, Oct. 1970.
Clark, Jr. Epilogue, Fed. Proc., vol. 29, No. 5, p. 1820, Oct. 1970.
Gollan et al., Experimental Pathology After Respiration and Injection of Various Fluorocarbon Liquids, Exp. Med and Surg. vol. 26, No. 4, Dec. 1968, pp. 249–262.
Clark Jr., et al., Survival of Mammals Breathing Organic Liquids Equilibrated with Oxygen at Atmospheric Pressure, Science vol. 152, pp. 1755–1756, Jun. 1966.

Primary Examiner—Henry J. Recla

[57] ABSTRACT

This invention relates to the combination of a number of pieces of separate functioning apparatus in order to accomplish the combined purposes of producing medical grade oxygen from air, saturating an inert isotonic liquid with the oxygen, adjusting the temperature of the oxygen saturated liquid to a predetermined temperature, injecting the oxygen saturated liquid into the bottom of the animal lung(s) cavity, circulating the liquid up through the lung(s) cavity by removal of the carbon dioxide saturated liquid at the top of the lung(s) cavity along with displaced from the lung(s) cavity non-miscible, aqueous liquid; separation of nonmiscible liquid, filtering of isotonic liquid for particulate removal, heat sterilization of isotonic liquid as well as stripping of remaining absorbed gases, particularly carbon dioxide ($CO_2$), cooling and temperature adjusting of isotonic liquid to predetermined desired temperature, and return of isotonic liquid to saturator for resaturation with oxygen and repeat cycle use. Remaining isotonic liquid in the lung(s) cavity, at end of treatment is removed by inverting animal sufficiently to raise the influent tube at bottom of lung(s) cavity above effluent tube and inflating lung(s) cavity with medical grade oxygen gas.

1 Claim, 1 Drawing Figure

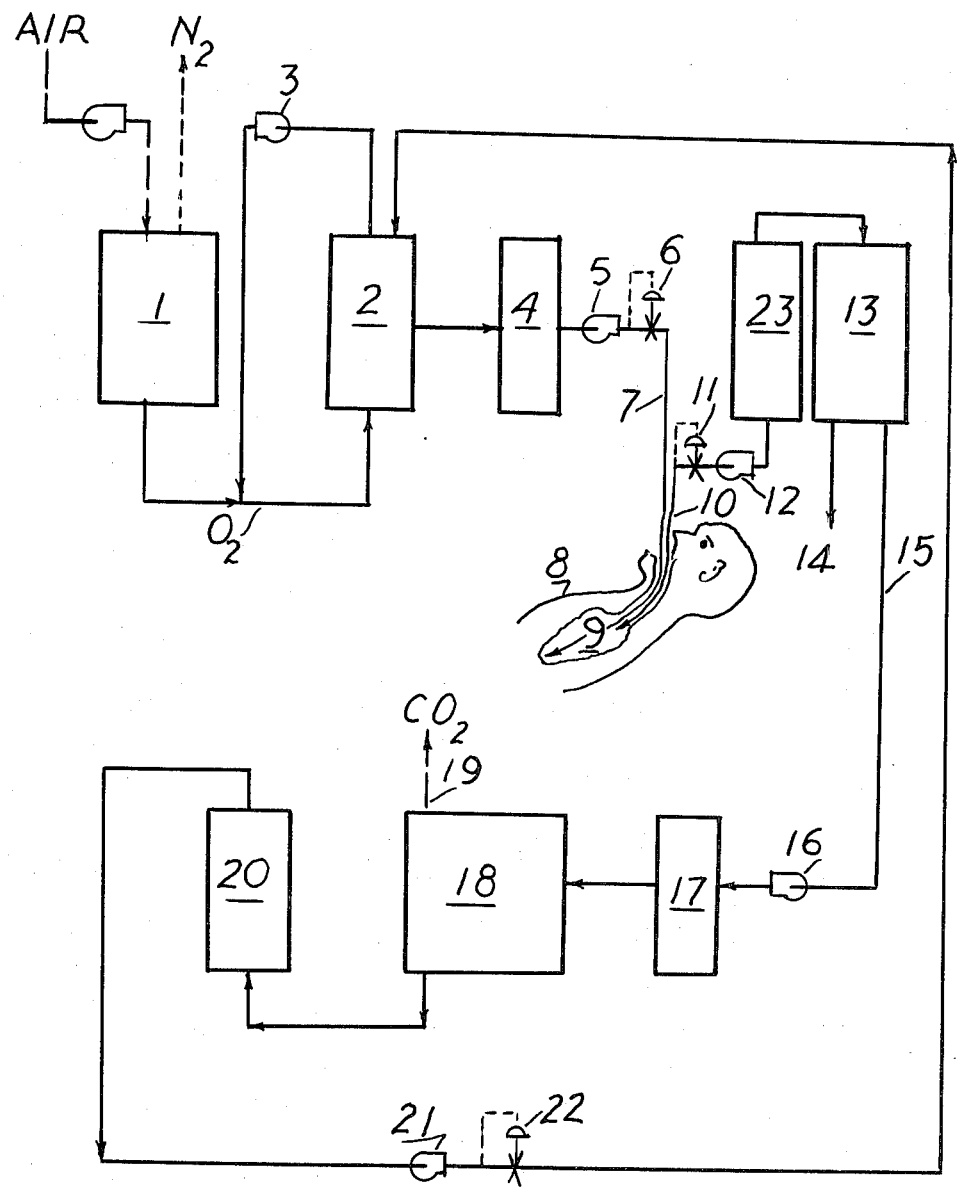

PORTABLE LUNG APPARATUS

This application is a continuation in part of Ser. No. 808,286 filed June 20, 1977; now abandoned.

BACKGROUND OF THE INVENTION AND PRIOR ART

The need of a synthetic blood has inspired Bio-Chemists and Biologists for a number of years. Dr. Leland C. Clark Jr., University of Cincinnati College of Medicine in 1966 found oxygen is highly soluble in liquid fluorochemicals and a potential synthetic blood. Whereas salt water or bood plasma dissolve about three (3) percent oxygen by volume and whole blood about (20) twenty percent, perfluorocarbons dissolve (40) forty percent or more; with carbon dioxide at least twice as soluble. Dr. Clark demonstrated this high oxygen solubility by submerging mice in inert liquid perfluorochemicals for extended periods. The animals were able to obtain sufficient oxygen by breathing the liquid and upon removal showed no ill effects. Intravenously injected perfluorochemicals can be lethal because they are immiscible with blood and can thus produce embolisms.

Emulsions of perfluorochemicals has been more successful as a blood substitute. Animals infused with these immediately began producing erythrocytes and blood proteins. By the time most of the perfluorochemical had been cleared from circulation, generally within a week, the animals had regenerated nearly all their erythrocytes. Materials found satisfactory for emulsions are perfluorotributylamine and perfluorobutyltetrahydrofuran, perfluorodecalin and perfluoromethyldecalin.

Leland Clark, also found, in 1966 at the Alabama Medical College that Silicone liquids as well as fluorocarbon liquids dissolve and hold about (20) twenty percent (by volume) oxygen. Dr. Clark's conclusion was that if animal organs and tissue such as lung(s) are sustained by the (20) twenty percent oxygen in air, they could be sustained by the (20) twenty percent oxygen in liquids. His conclusions were subsequently borne out by laboratory proof.

A number of factors must be kept in mind when considering breathing liquids. The lungs are functional organs not necessarily violated by the presence of liquid. In the lungs are millions of tiny capillaries. These transport the red blood cells to the tissue interface with the interior of the lung(s) for release by exchange the carbon dioxide for intake of oxygen. A liquid medium which can bring enough oxygen to the red blood cells and carry away enough carbon dioxide; will perform a normal exchange just as with air (fluid).

Drowning occurs for several reasons. Fresh water, even with adequate oxygen, is hypotonic, that is, it has less salt than the blood, and the osmotic pressure in the red cells admits too much water which expands and ruptures the cell. Salt water, even with adequate oxygen, is hypertonic, that is, it has more salt than the blood, and the osmotic pressure in the red cells loses too much water and destroys the cell. Hypertonic solutions also cause the larynx to go into spasm and the animal suffocates.

Research toward breathable liquids has progressed from pressurized saline to use of polyorganosiloxane(s) and fluorocarbon(s) liquids. An experimentally acceptable fluorocarbon has been the family of perfluorodecalin. The structure of this compound being two phenol rings side by side, with fluorine atoms replacing all hydrogen atoms ($C_{10}F_8$). Although perfluorodecaline is almost twice as heavy as water, test animals breath it in and out as well as air.

There is no past history or prior art for this invention.

REFERENCES

U.S. Patents

U.S. Pat. No. 2,616,927: Kauck, et al., May 12, 1950;
U.S. Pat. No. 2,594,272: Kauck, et al, Apr. 29, 1952;
U.S. Pat. No. 3,665,678: Kammermeyer, et al., May 30, 1972;
U.S. Pat. No. 3,762,133; Merriman, et al., Oct. 2, 1973;
U.S. Pat. No. 4,049,398; Vaseen, Sept. 20, 1977;
Application No. 891,548; filed Mar. 30, 1978: Vaseen: awarded, but not yet issued.

SUMMARY OF THE INVENTION

The primary object of this invention is to combine the functions of several types of apparatus into the single function of developing an artificial and mechanical portable lung exterior of the animal body.

The function of the external mechanical lung(s) apparatus that may produce a means of providing to the lung(s) cavity tissue a breathable liquid containing dissolved oxygen satisfactory to the particular animal and body weight requirements for oxygen, and cycling the spent oxygen depleted, now carbon dioxide saturated breathable liquid out of the lung apparatus for treatment required for recycle use.

This invention proposes that the oxygenated breathable liquid may be introduced into the lung(s) cavity by positive controlled means, such as a pump, through a tube carrying the breathable liquid to the bottom or lowest part of the lung(s) tissue (in the position the patient has been placed), and the oxygen spent, carbon dioxide charged liquid removed by aspirator tube and pump from a relatively higher or top location in the lung(s).

BRIEF DESCRIPTION OF THE DRAWING

1. Apparatus for "Producing Medical Grade Oxygen for Human, Animal, or Laboratory use by Paramagnetic Separation of Oxygen from air." U.S. Patent No. 4,150,956, dated, Apr. 24, 1979, (Originally application No. 891,548 filed Mar. 30, 1978), and U.S. Pat. No. 4,049,398; Vaseen: Sept. 20, 1977.

2. Saturator-apparatus for dissolving medical grade oxygen in the isotonic liquid.

3. Recycle pump for unabsorbed and/or surplus oxygen.

4. Temperature control and adjustment apparatus for both cooling and/or heating isotonic liquid.

5. Pump for transferring oxygen saturated isotonic liquid to bottom of lung(s) cavity of animal patient.

6. Influent flow rate and pressure control apparatus adjustable for animal patient requirements.

7. Influent tube carrying oxygen saturated isotonic liquid to bottom of lung(s) cavity.

8. Animal patient in semi-reclining position.

9. Animal patient lung(s) cavity.

10. Effluent tube removing both carbon dioxide saturated isotonic liquid, but also, non miscible aqueous matter such as mucus.

11. Effluent flow rate and pressure control apparatus adjustable to act in concert with flow rate and pressure control apparatus (6) above.

12. Pump for aspirating carbon dioxide saturated isotonic liquid and aqueous matter from top of lung(s) cavity of animal patient.

13. Centrifuge for separation of isotonic liquid from aqueous phases.

14. Discharge of centrifuge of aqueous phases to disposal.

15. Discharge of centrifuge of isotonic liquid to filter apparatus.

16. Transfer pump to move isotonic liquid from centrifuge through filter.

17. Filter to purify isotonic liquid by removal of suspended solids and and liquids particulates.

18. Sterilizer by heating of the isotonic liquid, which also strips the isotonic liquid of its soluble carbon dioxide and any trace oxygen due to low solubility of gases at sterilization temperature.

19. Carbon dioxide release from sterilizer to atmosphere.

20. Temperature adjustment apparatus to lower isotonic liquid from sterilization temperature to within temperature range of temperature adjustment apparatus. (4)

21. Transfer pump to return isotonic liquid to oxygen saturator (2).

22. Flow rate and pressure producing pump to adjust isotonic liquid flow rate to be in concert with pumps (5) and (12) as well as in concert with flow control apparatus (6) and (11).

23. Observation vessel.

PREFERRED EMBODIMENTS

This invention is concerned with the necessary combined apparatus for possible circulation through lung(s) cavity against the tissue, of live animals, with a breathable liquid.

The design example here described is based on the use of an apparatus combination which has a capacity for providing for example 0.5 grams of oxygen dissolved in an isotonic liquid per each minute of use, to an animal (8) with a gross body weight of up to 200 pounds, with a normal tidal breathing cycle of 500 cc, per each respiration.

For example, selection of an isotonic liquid which has an absorption ratio which will retain 0.20 liters of oxygen per each liter of isotonic liquid at 85° F. and atmospheric pressure.

In order to assure the use of sterile apparatus, preferably, the apparatus is designed for a period of use, then replaced with another unit, for instance, a period of one hour.

Based on a composite apparatus, preferably for one hour use, with an animal weight, as previously disclosed, the apparatus (1) for producing medical grade oxygen is designed to produce, preferably 30 grams of oxygen per hour. The saturator apparatus containing the necessary quantity of isotonic liquid required to absorb the 30 grams of oxygen per hour is actuated by first establishing the quantity of isotonic liquid contained in the absorber vessel (2). Saturation of the isotonic liquid with oxygen is accomplished second by operation of the recycle pump (3) which recirculates the unabsorbed oxygen from the top of the absorber vessel or saturator (2) back to the bottom of the vessel. Normal start up of the oxygen generator/producer apparatus (1) and saturator at building interior ambient temperature would be between 70° F. (21.11° C.) and 85° F. (29.44° C.); therefore, prior to filling the animal lung (9) cavity with the oxygen saturated isotonic breathable liquid, the isotonic liquid is preferably temperature adjusted in a cooler/heater apparatus (4). The temperature, preferably, is adjusted to within 0.1° F. of the body blood temperature. In specific instances where it is medically advantageous, the temperature is increased or decreased as desired by the treating medical authority in charge.

Two tubes (7) (10) may be inserted through the trachea and thence to each bronchus. A single preferably one cm. diameter flexible tube (7) will provide the required 10 liters per minute of isotonic liquid to the lung(s). Individual tubes to each lung will provide more flexibility of control as well as inspection of effluent flow. This can be provided by preferably dual 0.60 cm diameter tubes. The tubes may be threaded through the mouth, down the trachea and into each right and left bronchus. The tube should extend into the particular lobe requiring the greatest amount of treatment and to the lowest extremity possible.

Return tubes (10) may be inserted in like manner but extend preferably only to the entrance to each bronchus.

Pressure and flow control valve (6) is adjustable to allow the isotonic liquid fill the lung(s) cavity. As soon as the lung(s) have been expanded to the desired degree, that is, for a 150 pound animal, 1750 to 2000 cc per lung; the return pump (12) will remove the liquid at the entry from the trachea to the bronchus, and return it with pressure and flow control by valve (11) to an observation vessel (23) for visual observation and measurement of moisture and mucus quantity.

The effluent isotonic liquid, now saturated with absorbed carbon dioxide from the lung tissue discharge, along with mucus, carrying moisture and any particulate material can be separated from the non-miscible aqueous and other material which may be entrained with the isotonic liquid by centrifuge (13). The extraneous reject material (14) from the centrifuge can be disposed of to waste. The carbon dioxide saturated isotonic liquid is now transferred to a filter (17) which removes any remaining particulate material greater than, preferably, (1/10) one-tenth micron in diameter. The filtered isotonic liquid is now transferred to a sterilizer (18) which heats the liquid to, preferably, 300° F. (149° C.), or greater for preferably 10 minutes or longer. The carbon dioxide gas absorption capacity is at the sterilization temperature reduced to, for practical purposes, zero, thus stripping (19) the isotonic liquid of the carbon dioxide gas.

The isotonic liquid is then transferred through a temperature adjustment apparatus or heat exchanger (20) where it is cooled to the temperature of the influent isotonic liquid according to the animal lungs as controlled by temperature adjustment apparatus (4).

The composite apparatus has now completed one full cycle of operation which can be continued for an indefinite period, but preferably for one hour; then replaced with a new sterile composite apparatus.

Thus is disclosed and taught the art and science of composing several types of apparatus for the composed single purpose of creating an apparatus which can be used to replace the normal animal respiration of live animals with a mechanical lung or portable lung machine. Said apparatus or portable lung machine providing necessary respiratory oxygen from absorbed oxygen carried in a breathable liquid, to the lung(s) cavity, and respiratory carbon dioxide absorbed therein, from the lung(s) cavity.

I claim:

1. A composite mechanical lung machine, consisting of:

medical oxygen supply means;

isotonic, breathable liquid oxygen saturator means connected to said oxygen supply means for saturating isotonic, breathable liquid with oxygen from said supply means;

first heat exchanger means connected to said oxygen saturator means for temperature adjustment of the breathable liquid;

means for introducing said oxygen saturated isotonic liquid into animal lung(s) cavity;

means for removing said isotonic liquid from the animal lung(s) cavity;

first transfer pump means for transferring said isotonic, breathable liquid from said first heat exchanger means to said introducing means;

first flow and pressure control means connected between said first transfer pump means and said introducing means for controlling flow and pressure of said isotonic, breathable liquid to said introducing means;

separator means for separating said isotonic, breathable liquid from aqueous liquids accumulated from said lung(s) cavity;

second transfer pump means connected for transferring said isotonic, breathable liquid from said removing means to said separator means;

second flow and pressure control means connected between said second transfer pump means and said removing means for controlling flow and pressure of said isotonic, breathable liquid from said removing means;

filter means connected to said separator means for separation and removal of particulate solids from the isotonic, breathable liquid accumulated from the lunt(s) cavity;

heat exchange sterilizer means connected to said filter means for heat stripping absorbed carbon dioxide from the breathable liquid accumulated in the lung(s) cavity and sterilizing said breathable liquid;

second heat exchanger means connected to said sterilizer means for temperature adjustment of the breathable liquid from said sterilizer means to a selected body use temperature;

third transfer pump means for transferring said isotonic, breathable liquid from said second heat exchanger means to said oxygen saturator; and third flow and pressure control means connected between said third transfer pump means and said oxygen saturator means for controlling flow and pressure of said isotonic, breathable liquid from said third transfer pump means.

* * * * *